United States Patent
Jenson

(10) Patent No.: US 7,878,966 B2
(45) Date of Patent: Feb. 1, 2011

(54) VENTRICULAR ASSIST AND SUPPORT DEVICE

(75) Inventor: Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1203 days.

(21) Appl. No.: 11/051,113

(22) Filed: Feb. 4, 2005

(65) Prior Publication Data

US 2006/0178550 A1    Aug. 10, 2006

(51) Int. Cl.
*A61B 17/12*    (2006.01)

(52) U.S. Cl. .................................................. 600/16

(58) Field of Classification Search .................. 600/16, 600/17; 623/3.1
See application file for complete search history.

(56) References Cited

U.S. PATENT DOCUMENTS

| | | | |
|---|---|---|---|
| 3,671,979 A | 6/1972 | Moulopoulos | 3/1 |
| 4,291,420 A | 9/1981 | Reul | 3/1.5 |
| 4,621,617 A | 11/1986 | Sharma | 128/1 |
| 4,666,443 A | 5/1987 | Portner | 623/3 |
| 4,690,134 A | 9/1987 | Snyders | 128/64 |
| 4,787,901 A | 11/1988 | Baykut | 623/2 |
| 4,872,874 A | 10/1989 | Taheri | 623/1 |
| 4,902,273 A | 2/1990 | Choy et al. | 600/18 |
| 4,908,012 A | 3/1990 | Moise et al. | 600/16 |
| 4,935,030 A | 6/1990 | Alonso | 623/2 |
| 4,994,077 A | 2/1991 | Dobben | 623/2 |
| 5,002,567 A | 3/1991 | Bona et al. | 623/2 |
| 5,141,491 A | 8/1992 | Bowald | 604/22 |
| 5,163,953 A | 11/1992 | Vince | 623/2 |
| 5,219,355 A | 6/1993 | Parodi et al. | 606/191 |
| 5,254,127 A | 10/1993 | Wholey et al. | 606/153 |
| 5,327,774 A | 7/1994 | Nguyen et al. | 73/37 |
| 5,332,402 A | 7/1994 | Teitelbaum | 623/2 |
| 5,370,685 A | 12/1994 | Stevens | 623/2 |
| 5,411,552 A | 5/1995 | Anderson et al. | 623/2 |
| 5,469,868 A | 11/1995 | Reger | 128/898 |
| 5,480,423 A | 1/1996 | Ravenscroft et al. | 623/1 |
| 5,500,014 A | 3/1996 | Quijano et al. | 623/2 |
| 5,545,214 A | 8/1996 | Stevens | 623/2 |

(Continued)

FOREIGN PATENT DOCUMENTS

EP    0 380 666    8/1990

(Continued)

OTHER PUBLICATIONS

US 6,673,110, Jan. 2004, Alfieri et al. (withdrawn).

(Continued)

*Primary Examiner*—Michael Kahelin
(74) *Attorney, Agent, or Firm*—Brooks, Cameront & Huebsch, PLLC

(57) ABSTRACT

A ventricular assist device to provide cardiac assistance to a damaged ventricle chamber. The ventricular assist device is formed of an ventricle body which is anchorable to spaced ventricle wall portions to provide cardiac assistance. Operation of the ventricular assist device is timed or synchronized with the operating phases of the ventricle chamber. The ventricular assist device can be intravascularly deployed to provide a less invasive treatment procedure and can be adapted to provide static support if active assistance is no longer required.

7 Claims, 13 Drawing Sheets

U.S. PATENT DOCUMENTS

| | | | |
|---|---|---|---|
| 5,554,185 A | 9/1996 | Block et al. | 623/2 |
| 5,643,208 A | 7/1997 | Parodi | 604/96 |
| 5,693,087 A | 12/1997 | Parodi | 623/1 |
| 5,713,953 A | 2/1998 | Vallana et al. | 623/2 |
| 5,713,954 A | 2/1998 | Rosenberg et al. | 623/3 |
| 5,716,370 A | 2/1998 | Williamson, IV et al. | 606/153 |
| 5,735,859 A | 4/1998 | Fischell et al. | 606/108 |
| 5,741,326 A | 4/1998 | Solovay | 623/1 |
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,879,320 A | 3/1999 | Cazenave | 604/8 |
| 5,879,375 A | 3/1999 | Larson, Jr. et al. | 607/30 |
| 5,895,419 A | 4/1999 | Tweden et al. | 623/2 |
| 5,910,170 A | 6/1999 | Reimink et al. | 623/2 |
| 5,961,440 A * | 10/1999 | Schweich et al. | 600/16 |
| 6,010,531 A | 1/2000 | Donlon et al. | 623/2 |
| 6,042,607 A | 3/2000 | Williamson, IV et al. | 623/2 |
| 6,099,460 A | 8/2000 | Denker | 600/17 |
| 6,139,575 A | 10/2000 | Shu et al. | 623/2.12 |
| 6,287,334 B1 | 9/2001 | Moll et al. | 623/1.24 |
| 6,293,901 B1 | 9/2001 | Prem | 600/17 |
| 6,309,341 B1 | 10/2001 | Denker | 600/16 |
| 6,312,447 B1 | 11/2001 | Grimes | 606/219 |
| 6,338,712 B2 | 1/2002 | Spence et al. | 600/201 |
| 6,343,605 B1 * | 2/2002 | Lafontaine | 128/898 |
| 6,355,030 B1 | 3/2002 | Aldrich et al. | 606/28 |
| 6,402,780 B2 | 6/2002 | Williamson, IV et al. | 623/2.11 |
| 6,406,422 B1 | 6/2002 | Landesberg | 600/17 |
| 6,409,760 B1 | 6/2002 | Melvin | 623/3.1 |
| 6,419,696 B1 | 7/2002 | Ortiz et al. | 623/2.37 |
| 6,425,916 B1 | 7/2002 | Garrison et al. | 623/2.11 |
| 6,440,164 B1 | 8/2002 | DiMatteo et al. | 623/1.24 |
| 6,451,054 B1 | 9/2002 | Stevens | 623/2.11 |
| 6,454,799 B1 | 9/2002 | Schreck | 623/2.18 |
| 6,461,366 B1 | 10/2002 | Seguin | 606/144 |
| 6,503,272 B2 | 1/2003 | Duerig et al. | 623/1.24 |
| 6,508,833 B2 | 1/2003 | Pavcnik et al. | 623/1.15 |
| 6,511,413 B2 | 1/2003 | Landesberg | 600/17 |
| 6,564,805 B2 | 5/2003 | Garrison et al. | 128/898 |
| 6,569,196 B1 | 5/2003 | Vesely | 623/2.14 |
| 6,572,533 B1 | 6/2003 | Shapland et al. | 600/37 |
| 6,592,619 B2 | 7/2003 | Melvin | 623/3.11 |
| 6,602,286 B1 | 8/2003 | Strecker | 623/1.24 |
| 6,629,534 B1 | 10/2003 | St. Goar et al. | 128/898 |
| 6,635,085 B1 | 10/2003 | Caffey et al. | 623/2.1 |
| 6,666,885 B2 | 12/2003 | Moe | 623/2.12 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,475 B2 | 1/2004 | Cox et al. | 600/37 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,709,382 B1 | 3/2004 | Horner | 600/16 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,746,471 B2 | 6/2004 | Mortier et al. | 606/207 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |

| Patent/Pub. No. | Date | Inventor | Class |
|---|---|---|---|
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,953,332 B1 | 10/2005 | Kurk et al. | 425/275 |
| 2002/0013571 A1 | 1/2002 | Goldfarb et al. | 606/1 |
| 2002/0026216 A1 | 2/2002 | Grimes | 606/213 |
| 2002/0082630 A1 | 6/2002 | Menz et al. | 606/167 |
| 2002/0123802 A1 | 9/2002 | Snyders | 623/2.18 |
| 2002/0151970 A1 | 10/2002 | Garrison et al. | 623/2.11 |
| 2002/0183835 A1 | 12/2002 | Taylor et al. | 623/2.11 |
| 2002/0183838 A1 | 12/2002 | Liddicoat et al. | 623/2.11 |
| 2002/0198594 A1 | 12/2002 | Schreck | 623/2.11 |
| 2003/0050694 A1 | 3/2003 | Yang et al. | 623/2.11 |
| 2003/0130729 A1 | 7/2003 | Paniagua et al. | 623/2.11 |
| 2003/0163194 A1 | 8/2003 | Quijano et al. | 623/2.11 |
| 2003/0167071 A1 | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015040 A1 | 1/2004 | Melvin | 600/16 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024286 A1 | 2/2004 | Melvin | 600/16 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0172077 A1 | 9/2004 | Chinchoy | 607/17 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Lobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/2.11 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |

| Publication No. | Date | Inventor | Class |
|---|---|---|---|
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0249452 A1 | 12/2004 | Adams et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0049679 A1 | 3/2005 | Taylor et al. | 623/1.15 |
| 2005/0049692 A1 | 3/2005 | Numamoto et al. | 623/1.24 |
| 2005/0049696 A1 | 3/2005 | Siess et al. | 623/2.11 |
| 2005/0049697 A1 | 3/2005 | Sievers | 623/2.26 |
| 2005/0054977 A1 | 3/2005 | Laird et al. | 604/96.01 |
| 2005/0055079 A1 | 3/2005 | Duran | 623/1.13 |
| 2005/0055087 A1 | 3/2005 | Starksen | 623/2.11 |
| 2005/0055088 A1 | 3/2005 | Liddicoat et al. | 623/2.11 |
| 2005/0055089 A1 | 3/2005 | Macoviak et al. | 623/2.37 |
| 2005/0060029 A1 | 3/2005 | Le et al. | 623/2.11 |
| 2005/0060030 A1 | 3/2005 | Lashinski et al. | 623/2.37 |
| 2005/0065460 A1 | 3/2005 | Laird | 604/20 |
| 2005/0065550 A1 | 3/2005 | Starksen et al. | 606/219 |
| 2005/0065594 A1 | 3/2005 | Dimatteo et al. | 623/1.24 |
| 2005/0065597 A1 | 3/2005 | Lansac | 623/2.11 |
| 2005/0070998 A1 | 3/2005 | Rourke et al. | 623/2.11 |
| 2005/0075584 A1 | 4/2005 | Cali | 600/587 |
| 2005/0075659 A1 | 4/2005 | Realyvasquez et al. | 606/167 |
| 2005/0075662 A1 | 4/2005 | Pedersen et al. | 606/194 |
| 2005/0075712 A1 | 4/2005 | Biancucci et al. | 623/1.11 |
| 2005/0075713 A1 | 4/2005 | Biancucci et al. | 623/1.11 |
| 2005/0075717 A1 | 4/2005 | Nguyen et al. | 623/1.26 |
| 2005/0075718 A1 | 4/2005 | Nguyen et al. | 623/1.26 |
| 2005/0075719 A1 | 4/2005 | Bergheim | 623/1.26 |
| 2005/0075720 A1 | 4/2005 | Nguyen et al. | 623/1.26 |
| 2005/0075723 A1 | 4/2005 | Schroeder et al. | 623/2.1 |
| 2005/0075724 A1 | 4/2005 | Svanidze et al. | 623/2.11 |
| 2005/0075725 A1 | 4/2005 | Rowe | 623/2.14 |
| 2005/0075726 A1 | 4/2005 | Svanidze et al. | 623/2.14 |
| 2005/0075728 A1 | 4/2005 | Nguyen et al. | 623/2.17 |
| 2005/0075729 A1 | 4/2005 | Nguyen et al. | 623/2.18 |
| 2005/0075730 A1 | 4/2005 | Myers et al. | 623/2.18 |
| 2005/0075731 A1 | 4/2005 | Artof et al. | 623/2.18 |
| 2005/0080483 A1 | 4/2005 | Solem et al. | 623/2.11 |
| 2005/0085900 A1 | 4/2005 | Case et al. | 623/1.24 |
| 2005/0085903 A1 | 4/2005 | Lau | 623/2.11 |
| 2005/0085904 A1 | 4/2005 | Lemmon | 623/2.11 |
| 2005/0090846 A1 | 4/2005 | Pedersen et al. | 606/159 |
| 2005/0096735 A1 | 5/2005 | Hojeibane et al. | 623/1.24 |
| 2005/0096738 A1 | 5/2005 | Cali et al. | 623/2.18 |
| 2005/0096739 A1 | 5/2005 | Cao | 623/2.19 |
| 2005/0096740 A1 | 5/2005 | Langberg et al. | 623/2.36 |
| 2005/0101975 A1 | 5/2005 | Nguyen et al. | 606/151 |
| 2005/0102026 A1 | 5/2005 | Turner et al. | 623/2.1 |
| 2005/0107810 A1 | 5/2005 | Morales et al. | 606/143 |
| 2005/0107811 A1 | 5/2005 | Starksen et al. | 606/143 |
| 2005/0107812 A1 | 5/2005 | Starksen et al. | 606/143 |
| 2005/0107872 A1 | 5/2005 | Mensah et al. | 623/2.14 |
| 2005/0113910 A1 | 5/2005 | Paniagua et al. | 623/2.14 |
| 2005/0119673 A1 | 6/2005 | Gordon et al. | 606/151 |
| 2005/0119734 A1 | 6/2005 | Spence et al. | 623/2.11 |
| 2005/0119735 A1 | 6/2005 | Spence et al. | 623/2.36 |
| 2005/0125011 A1 | 6/2005 | Spence et al. | 606/144 |
| 2005/0131438 A1 | 6/2005 | Cohn | 606/170 |
| 2005/0137449 A1 | 6/2005 | Nieminen et al. | 600/37 |
| 2005/0137450 A1 | 6/2005 | Aronson et al. | 600/37 |
| 2005/0137451 A1 | 6/2005 | Gordon et al. | 600/37 |
| 2005/0137676 A1 | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1 | 6/2005 | Salahieh et al. | 623/2.11 |
| 2005/0137688 A1 | 6/2005 | Salahieh et al. | 623/2.11 |
| 2005/0137689 A1 | 6/2005 | Salahieh et al. | 623/2.11 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |
| 2005/0137694 A1 | 6/2005 | Haug et al. | 623/2.11 |
| 2005/0137696 A1 | 6/2005 | Salahieh et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |

| Pub. No. | Date | Inventor | Class |
|---|---|---|---|
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |

FOREIGN PATENT DOCUMENTS

| | | |
|---|---|---|
| EP | 0 466 518 | 1/1992 |
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 99/04724 | 2/1999 |
| WO | WO 00/66196 * | 11/2000 |
| WO | WO 00/67679 | 11/2000 |
| WO | WO 01/15650 | 3/2001 |
| WO | WO 01/17462 | 3/2001 |
| WO | WO 03/047468 | 6/2003 |
| WO | WO 03/084443 | 10/2003 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |
| WO | WO 2004/045378 | 6/2004 |
| WO | WO 2004/045463 | 6/2004 |
| WO | WO 2004/047677 | 6/2004 |
| WO | WO 2004/060217 | 7/2004 |
| WO | WO 2004/060470 | 7/2004 |
| WO | WO 2004/062725 | 7/2004 |
| WO | WO 2004/066803 | 8/2004 |
| WO | WO 2004/066826 | 8/2004 |
| WO | WO 2004/069287 | 8/2004 |
| WO | WO 2004/075789 | 9/2004 |
| WO | WO 2004/080352 | 9/2004 |
| WO | WO 2004/082523 | 9/2004 |
| WO | WO 2004/082527 | 9/2004 |
| WO | WO 2004/082528 | 9/2004 |
| WO | WO 2004/082536 | 9/2004 |
| WO | WO 2004/082537 | 9/2004 |
| WO | WO 2004/082538 | 9/2004 |
| WO | WO 2004/082757 | 9/2004 |
| WO | WO 2004/084746 | 10/2004 |
| WO | WO 2004/084770 | 10/2004 |
| WO | WO 2004/089246 | 10/2004 |
| WO | WO 2004/089250 | 10/2004 |
| WO | WO 2004/089253 | 10/2004 |
| WO | WO 2004/091449 | 10/2004 |
| WO | WO 2004/091454 | 10/2004 |
| WO | WO 2004/093638 | 11/2004 |
| WO | WO 2004/093726 | 11/2004 |
| WO | WO 2004/093728 | 11/2004 |
| WO | WO 2004/093730 | 11/2004 |
| WO | WO 2004/093745 | 11/2004 |
| WO | WO 2004/093935 | 11/2004 |
| WO | WO 2004/096100 | 11/2004 |
| WO | WO 2004/103222 | 12/2004 |
| WO | WO 2004/103223 | 12/2004 |
| WO | WO 2004/105584 | 12/2004 |
| WO | WO 2004/105651 | 12/2004 |
| WO | WO 2004/112582 | 12/2004 |
| WO | WO 2004/112585 | 12/2004 |
| WO | WO 2004/112643 | 12/2004 |
| WO | WO 2004/112652 | 12/2004 |
| WO | WO 2004/112657 | 12/2004 |
| WO | WO 2004/112658 | 12/2004 |
| WO | WO 2005/000152 | 1/2005 |
| WO | WO 2005/002424 | 1/2005 |
| WO | WO 2005/002466 | 1/2005 |
| WO | WO 2005/004753 | 1/2005 |
| WO | WO 2005/007017 | 1/2005 |
| WO | WO 2005/007018 | 1/2005 |
| WO | WO 2005/007036 | 1/2005 |
| WO | WO 2005/007037 | 1/2005 |
| WO | WO 2005/009285 | 2/2005 |
| WO | WO 2005/009286 | 2/2005 |
| WO | WO 2005/009505 | 2/2005 |
| WO | WO 2005/009506 | 2/2005 |
| WO | WO 2005/011473 | 2/2005 |
| WO | WO 2005/011534 | 2/2005 |
| WO | WO 2005/011535 | 2/2005 |
| WO | WO 2005/013860 | 2/2005 |
| WO | WO 2005/018507 | 3/2005 |
| WO | WO 2005/021063 | 3/2005 |
| WO | WO 2005/023155 | 3/2005 |
| WO | WO 2005/025644 | 3/2005 |
| WO | WO 2005/027790 | 3/2005 |
| WO | WO 2005/027797 | 3/2005 |
| WO | WO 2005/034812 | 4/2005 |
| WO | WO 2005/039428 | 5/2005 |
| WO | WO 2005/039452 | 5/2005 |
| WO | WO 2005/046488 | 5/2005 |
| WO | WO 2005/046528 | 5/2005 |
| WO | WO 2005/046529 | 5/2005 |
| WO | WO 2005/046530 | 5/2005 |
| WO | WO 2005/046531 | 5/2005 |
| WO | WO 2005/048883 | 6/2005 |
| WO | WO 2005/049103 | 6/2005 |
| WO | WO 2005/051226 | 6/2005 |
| WO | WO 2005/055811 | 6/2005 |
| WO | WO 2005/055883 | 6/2005 |
| WO | WO 2005/058206 | 6/2005 |
| WO | WO 2005/065585 | 7/2005 |
| WO | WO 2005/065593 | 7/2005 |
| WO | WO 2005/065594 | 7/2005 |
| WO | WO 2005/070342 | 8/2005 |
| WO | WO 2005/070343 | 8/2005 |
| WO | WO 2005/072654 | 8/2005 |
| WO | WO 2005/072655 | 8/2005 |
| WO | WO 2005/079706 | 9/2005 |
| WO | WO 2005/082288 | 9/2005 |
| WO | WO 2005/082289 | 9/2005 |
| WO | WO 2005/084595 | 9/2005 |
| WO | WO 2005/087139 | 9/2005 |
| WO | WO 2005/087140 | 9/2005 |

OTHER PUBLICATIONS

US 6,723,117, Apr. 20, 2004, Menz, et al. (withdrawn).

* cited by examiner

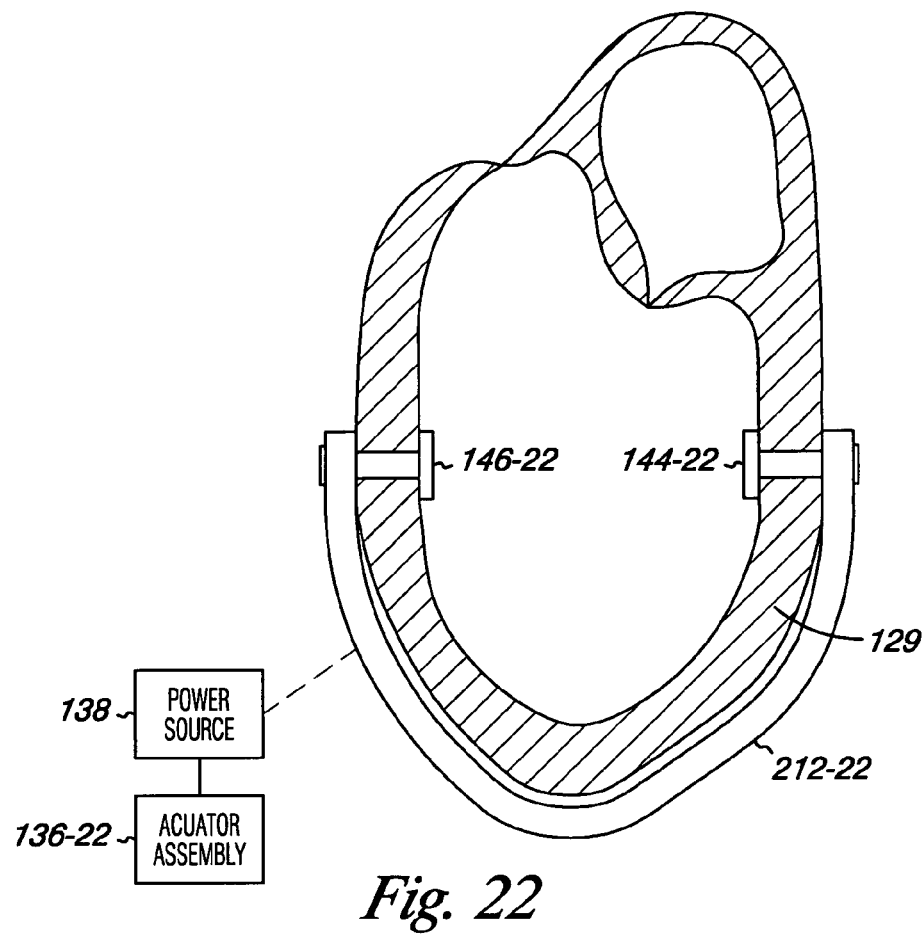
*Fig. 22*
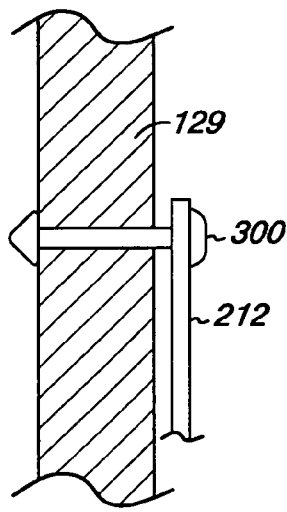 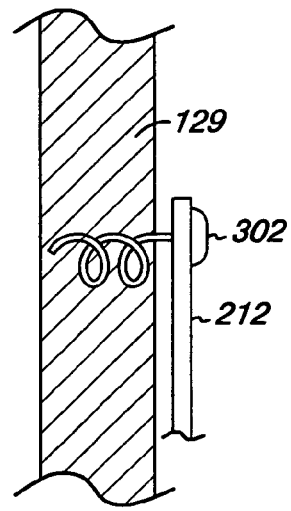 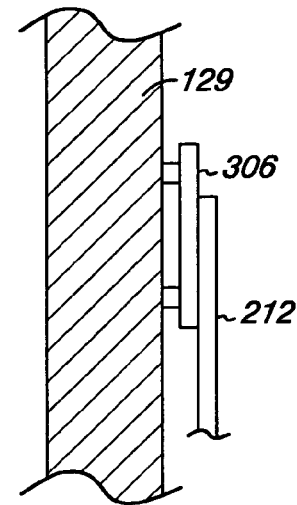
*Fig. 22-1*  *Fig. 22-2*  *Fig. 22-3*

VENTRICULAR ASSIST AND SUPPORT DEVICE

BACKGROUND OF THE INVENTION

The present invention relates to a cardiac device for treating cardiac disease. In particular, the present invention relates to a cardiac assist device for assisting with the blood pumping action of the heart.

The heart pumps blood to the body from chambers of the heart. In particular, blood is pumped from a right ventricle through a pulmonary valve into the pulmonary artery for oxygenation by the lungs. Oxygenated blood flows into the left ventricle and is pumped from the left ventricle throughout the body. Blood flows into the ventricle chambers during a diastole phase where the ventricle chamber is dilated or relaxed and is pumped from the ventricle chamber during a systole phase when the heart muscle is contracted.

The walls or muscle of a diseased heart can interfere with expansion or contraction of the heart or ventricles for systolic and diastolic phases. In particular, a diseased heart may include areas of non-contracting tissue, caused for example by a myocardial infraction, a hypoperfused area, or area of localized tissue death or necrosis. The non-contracting tissue may interfere with effective pumping during systole. In addition, a diseased heart may include areas that do not expand during diastole, thereby preventing proper filling of the ventricle chamber in preparation for the next systolic phase. Embodiments of the present invention provide solutions to these and other problems and offer advantages over the prior art.

SUMMARY OF THE INVENTION

The present invention relates to a ventricular assist device to provide cardiac assistance to a damaged ventricle chamber. The ventricular assist device is formed of a ventricular body which is anchorable to spaced ventricle wall portions to provide cardiac assistance. Operation of the ventricular assist device is timed or synchronized with the operating phases of the ventricle chamber. The ventricular assist device can be intravascularly deployed to provide a less invasive treatment procedure and can be adapted to provide static support if active assistance is no longer required.

BRIEF DESCRIPTION OF THE DRAWINGS

FIG. 22 schematically illustrates an embodiment of a ventricular assist device.

FIGS. 22-1 through 22-3 schematically illustrate an embodiment for connecting or attaching a ventricular assist device to a ventricle wall.

DETAILED DESCRIPTION OF THE PREFERRED EMBODIMENTS

Figure 1:
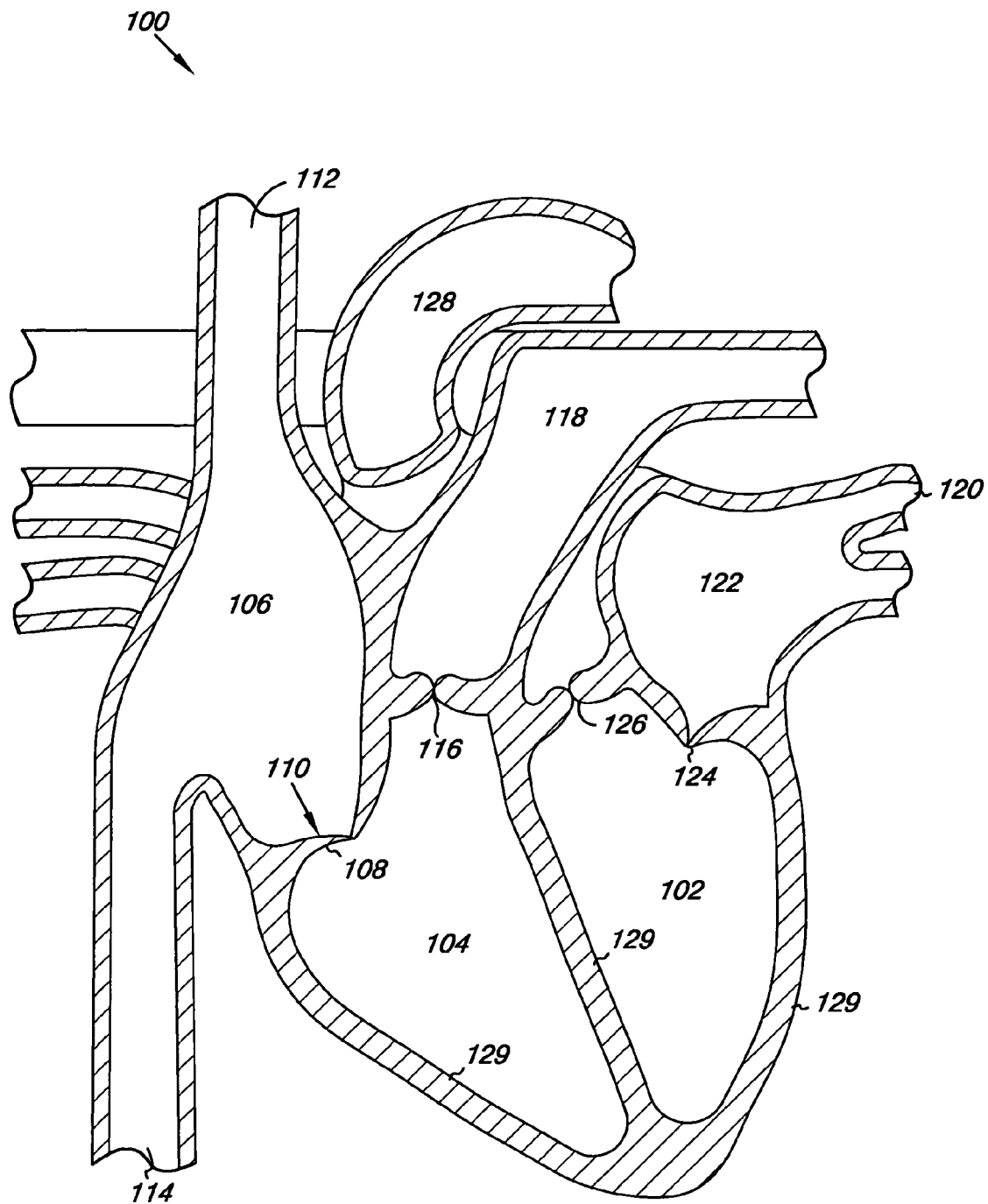
FIG. 1 is an illustration of a heart.

FIG. 1 is a sectional view of a heart 100 illustrating the left ventricle 102 and right ventricle 104 chambers of the heart. The left and right ventricles 102, 104 pump blood through the circulatory system of the body. In particular, blood is pumped from the right ventricle 104 to the pulmonary system for oxygenation and oxygenated blood is pumped from the left ventricle 102 throughout the body.

As shown in FIG. 1, blood is supplied to the right ventricle 104 from the right atrium 106 through tricuspid valve 108 as illustrated by arrow 110. Blood flows into the right atrium 106 from the superior vena cava 112 and inferior vena cava 114. Blood is pumped from the right ventricle 104 through pulmonary valve 116 into the pulmonary artery 118 for oxygenation. Oxygenated blood returns via the pulmonary veins 120 and is pumped from the left ventricle 102 for distribution throughout the body. In particular, oxygenated blood is supplied to the left atrium 122 and flows into of the left ventricle 102 through a mitral valve 124. Blood is pumped from the left ventricle 102 through aortic valve 126 through the aorta 128 for distribution throughout the body.

The chambers of the left and right ventricles 102, 104 are enclosed by ventricle walls 129 which during a diastolic phase relax and dilate to fill the chamber with blood. During a systolic phase, the walls or muscle contract to pump blood for distribution as previously discussed. The walls of a diseased heart may include areas of non-contracting tissue which interferes with the pumping action of the heart.

An area of non-contracting tissue may comprise a myocardial infraction or fibrous scarred tissue. Areas of non-contracting tissue may be caused by ischemia which is a decreased supply of blood to an area of tissue. Non-contracting tissue may also be the result of idiopathic disease or areas of necrosis or localized tissue death. An area of non-contracting tissue may also comprise tissue which is hibernating due to reduced blood flow to the affected tissue.

Figure 2:
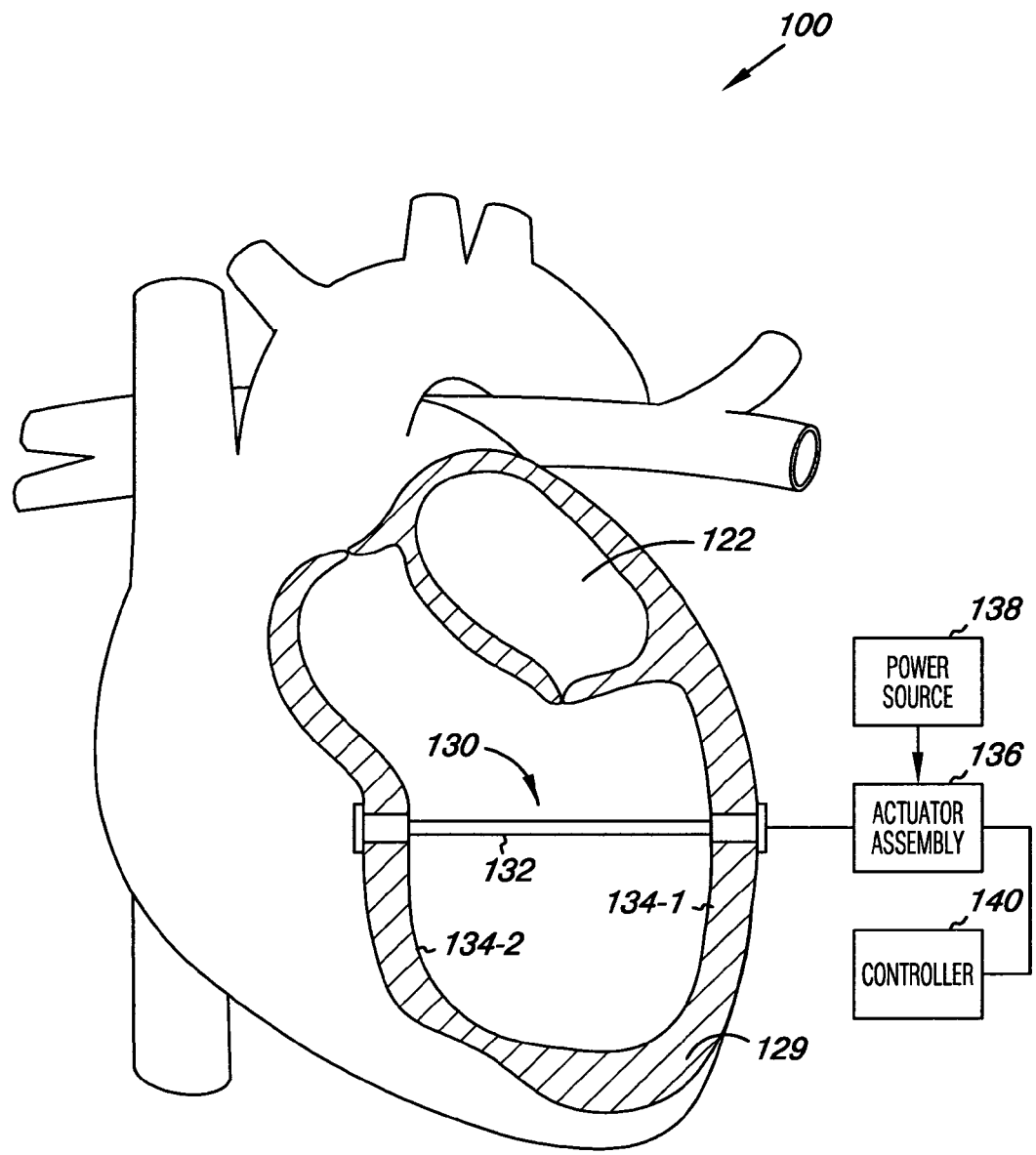
FIG. 2 is an illustration of an embodiment of a ventricular assist device of the present invention deployed in a ventricle chamber.

FIG. 2 schematically illustrates an embodiment of a ventricular assist device 130 of the present invention. As shown, the ventricular assist device 130 includes an elongate body 132 transventricularly disposed and having an adjustable length dimension between opposed ventricular wall portions 134-1, 134-2 as illustrated by dotted lines in FIG. 2. As illustrated schematically, an actuator assembly 136 is coupled to the elongate body 132 and to a power or energy source 138 to expand or collapse the length of the elongate body 132 to provide cardiac assistance to expand or contract the ventricle chamber for operation. As shown, the actuator assembly 136 is coupled to a controller 140 to time or synchronize actuation of the elongate body 132 to the pumping (diastolic and systolic) phases of the heart.

In one embodiment, the ventricular assist device can be transluminally implanted or inserted into the ventricular chamber for use, for example through a femoral artery as will be described. The schematically illustrated actuator assembly can be external or internally implanted and the power source can be an implantable power source or external power source. In a preferred embodiment, controller 140 receives input from sensing apparatus (not shown) which senses contraction and dilatation of the heart to time or synchronize operation of the assist device 130. Such sensing apparatus can include electrical, displacement pressure, or other sensing.

Figure 3:
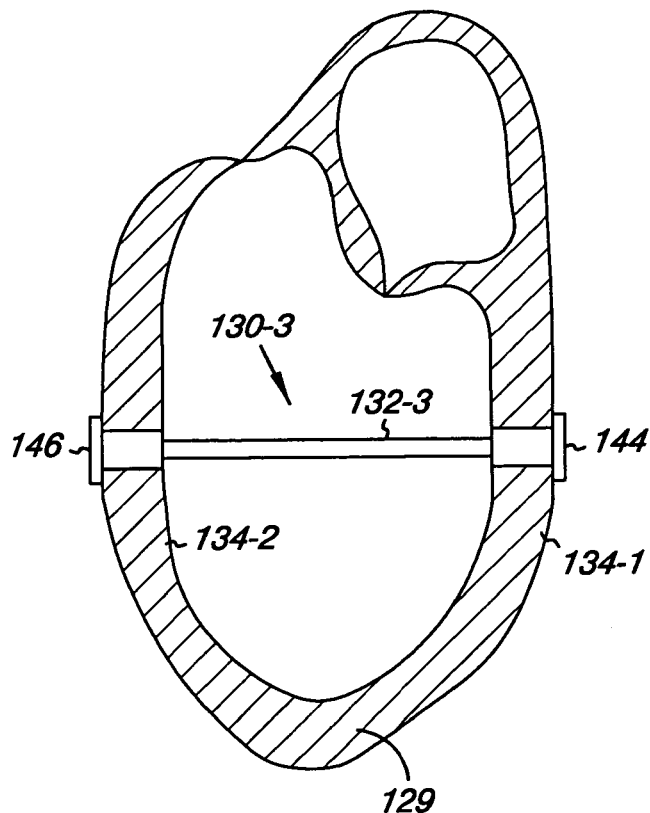
FIGS. 3-4 illustrate an embodiment of a ventricular assist device having an expanded length dimension (FIG. 3) and a contracted length dimension (FIG. 4) to provide ventricle assistance.
Figure 4:
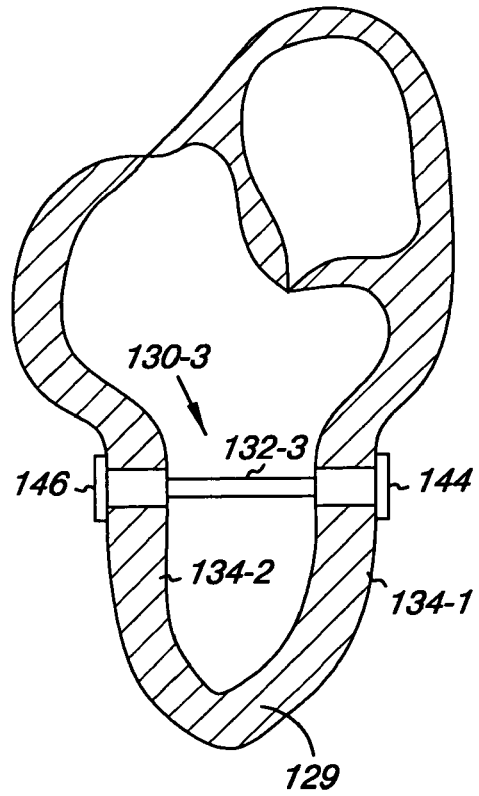

FIGS. 3-4 comparatively illustrate an embodiment of a ventricular assist device 130-3 having an elongate body 132-3 extending between opposed spaced ventricle anchors 144, 146 which are anchorable to opposed or spaced ventricle wall portions 134-1, 134-2 so that the elongate body extends across the ventricle chamber between opposed ventricle wall portions 134-1, 134-2 (i.e., transventricularly disposed). The elongate body 132-3 has an adjustable length dimension between the opposed spaced ventricle anchors 144, 146 to provide cardiac assistance to expand and/or contract the ventricle chamber for operation.

Thus, as shown in FIG. 3, during the diastolic phase, the length of the elongate body 132-3 is extended so that the ventricle chamber fills and as shown in FIG. 4, during a systolic phase, the length of the elongate body 132-3 is contracted to assist contraction of the ventricle walls to pump blood from the ventricle chamber. The length of the elongate body 132-3 is adjusted via an actuator assembly 136 as illustrated schematically in FIG. 2. Anchor devices 144, 146 are schematically illustrated and it should be understood that application of the present invention is not limited to any particular ventricle anchor device.

Figure 5:
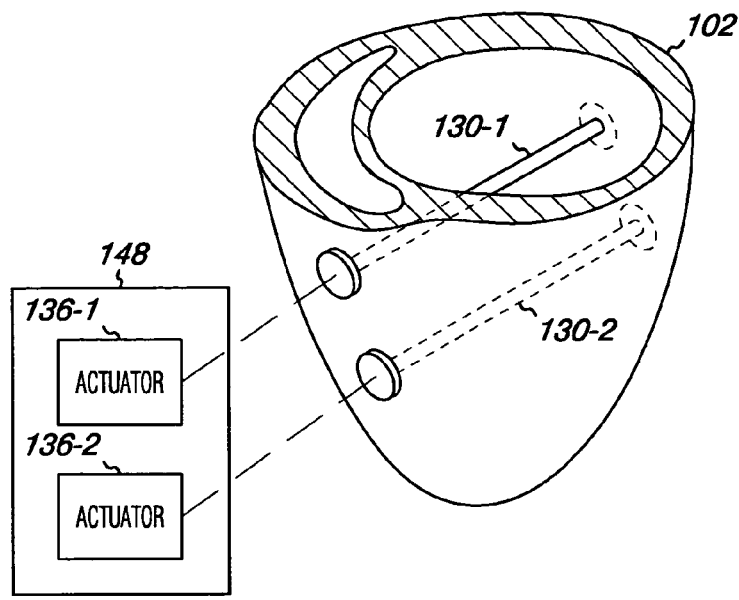
FIG. 5 illustrates a ventricle chamber including a plurality of ventricular assist devices.

As illustrated in FIG. 5, ventricle or cardiac assistance can be provided by multiple or a plurality of ventricular assist devices 130-1, 130-2 cooperatively actuated to assist pumping operation of the ventricle chamber. In particular, in the embodiment shown, multiple transversely deployed devices extend across the ventricle chamber between opposed ventricle wall portions to provide cardiac assistance. An actuator assembly 136-1, 136-2 is coupled to each device 130-1, 130-2 and are synchronously powered as illustrated by block 148 to mimic pumping operation of the ventricle chamber. The synchronous operation may be simultaneous or concurrent operation, or there may be a time delay so that one ventricular assist device is actuated slightly earlier than another ventricular assist device. In this way a coordinated contraction can be obtained in a more efficient and effective manner, better coordinated with natural ventricle contraction.

In assisting the pumping action of the chamber, the ventricular assist device(s) 130 exert expansive force to aid diastolic filling of the ventricle, or contraction force to aid systolic pumping of the ventricle, or both. Although a particular number of ventricular assist devices 130-1, 130-2 is shown, application of the present invention is not limited to the particular number or orientation shown nor a particular number or multiple separate actuators as shown.

Figure 6:
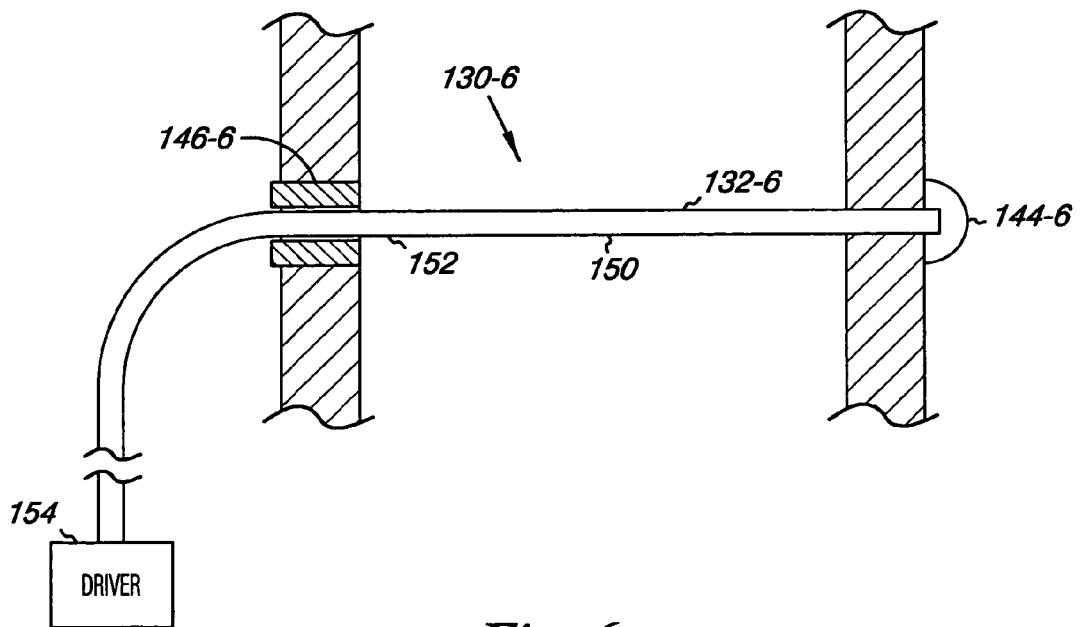
FIG. 6 illustrates an embodiment of a ventricular assist device including an elongate body having an adjustable length dimension between opposed spaced ventricle anchors.

FIG. 6 illustrates an embodiment of a ventricular assist device 130-6 for ventricle pumping assistance. In the embodiment illustrated in FIG. 6, the elongated body 132-6 includes a cable 150 having a ventricle anchor 144-6 fixed to an end thereof. The cable 150 is slidably disposed through channel 152 of a sleeve portion of anchor 146-6 to define the elongate body 132-6 having an adjustable length portion or dimension between spaced ventricle anchors 144-6, 146-6 or ventricle wall portions. A driver 154 illustrated schematically is energized to move cable 150 along an actuation stroke to expand and contract the length dimension between ventricle anchors 144-6, 146-6. For example, driver 152 can be pneumatically, hydraulically, electrically or magnetically powered to move cable 150 along the actuation stroke for pumping operation.

Figure 7:
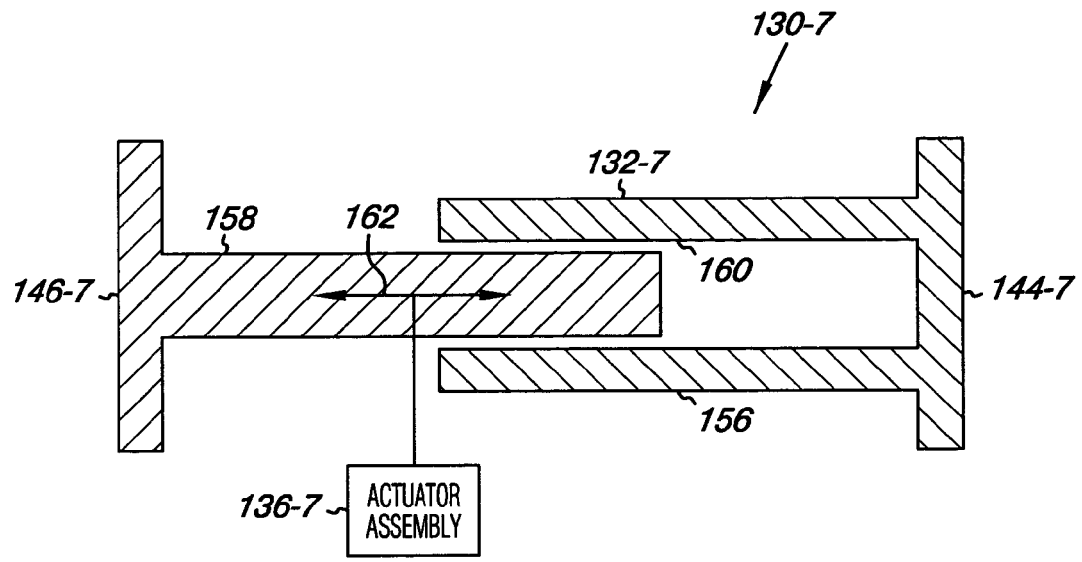
FIG. 7 schematically illustrates an alternate embodiment of a ventricular assist device including an elongate body having an adjustable length dimension between opposed spaced ventricle anchors.
Figure 8:
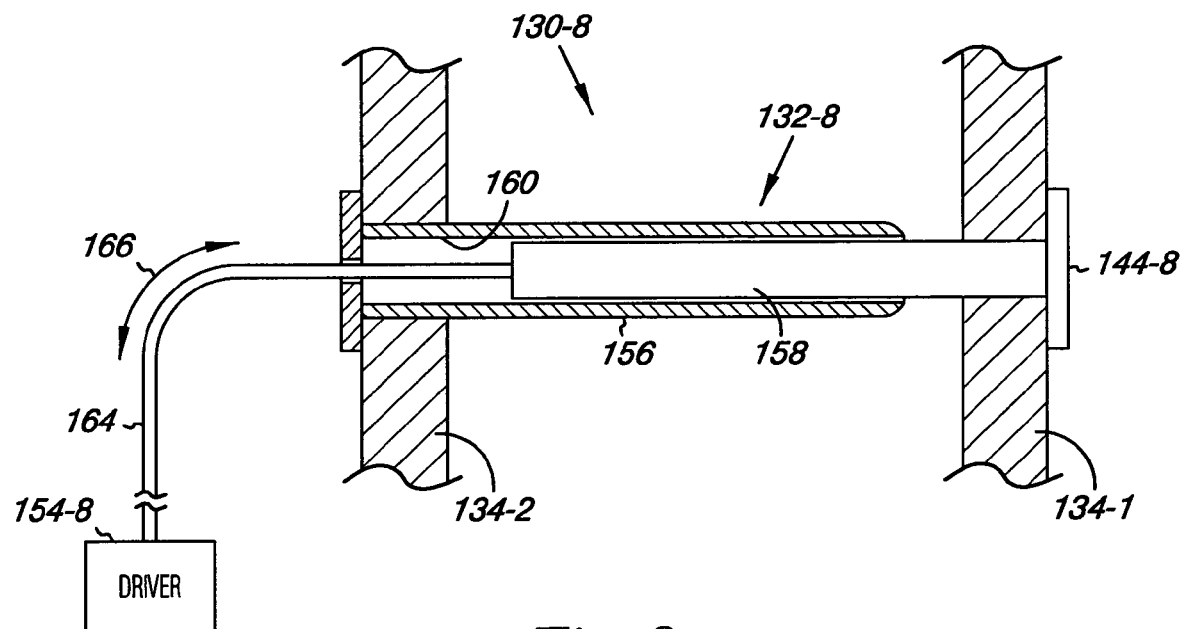
FIGS. 8-11 illustrate alternate embodiments of a ventricular assist device having an actuatable length dimension to provide ventricle assistance.

FIG. 7 illustrates an embodiment of a ventricular assist device 130-7 including an elongate body 132-7 having a first tubular body portion 156 and a second body portion 158 slidably disposed in a lumen 160 of the first body portion 156 to provide the adjustable length dimension. As shown, ventricle anchors 144-7, 146-7 are fixed to the first and second body portions 156, 158 respectively and the second body portion 158 is slidable relative to the first body portion 156 as illustrated by arrow 162 to form the elongated body 132-7 having an adjustable length dimension between ventricle anchors 144-7, 146-7. In the embodiment shown, the elongate body 132-7 is actuated between an expanded length dimension and a contracted length dimension via an actuator assembly 136-7 to slidably adjust the position of body portion 158 relative to body portion 156 to provide ventricular cardiac assistance.

FIGS. 8-11 illustrate alternate embodiments of a ventricular assist device including an elongate body having first and second body portions 156, 158 slideable relative to one another. In the embodiment illustrated in FIG. 8, the second body portion 158 is slideably adjusted relative to the first body portion 156 along an actuation stroke via a cable 164 coupled to a driver 154-8. Cable 164 is coupled to the second body portion 158 and driver 154-8. Driver 154-8 is energized by a power source (not shown) to move the cable 164 along an actuation stroke as illustrated by arrow 166 to expand and contract the length dimension of the elongate body 132-8. Driver 154-8 can be pneumatically, hydraulically, mechanically, electrically or magnetically powered. For example, the driver can include a pneumatic pump which is coupled to the cable, a motor assembly or the device can be actuated via a piezoelectric or shape memory material.

Figure 9:
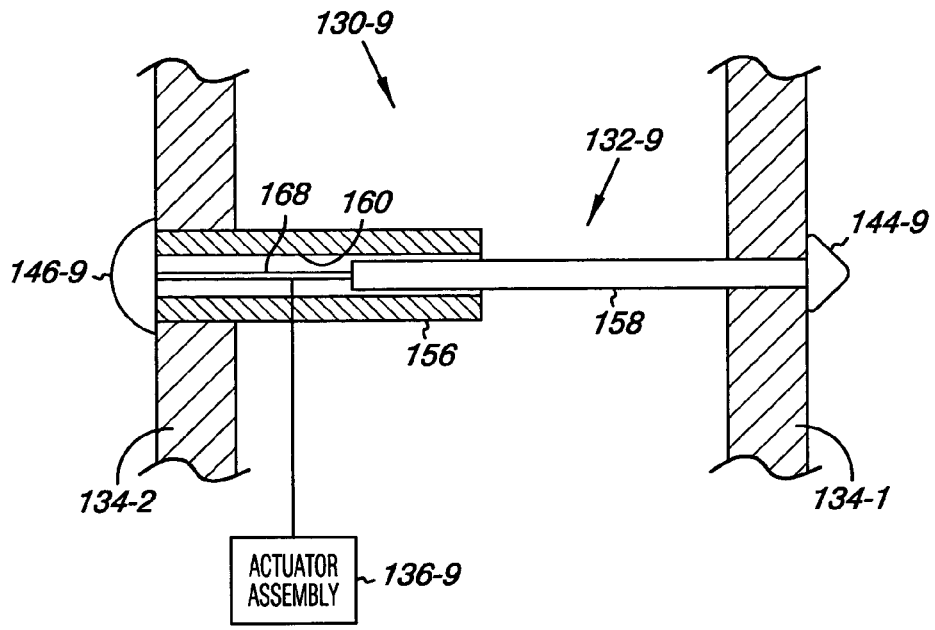

FIG. 9 illustrates an alternate embodiment of a ventricular assist device 130-9 including an elongate body 132-9 having slidable body portions 156, 158, as previously described. As shown, the elongate body 132-9 is transventricularly disposed and anchored relative to opposed ventricle wall portions as shown. In the illustrated embodiment body portion 158 is slidably adjusted relative to body portion 156 via an actuator assembly 136-9 including an internally disposed actuator 168 (illustrated schematically) in lumen 160 between the body portions 156, 158 to slidably move body portion 158 relative to body portion 156.

Actuator 168 is moved along an actuation stroke pneumatically, hydraulically, magnetically or electrically to slidably adjust body portion 158 relative to body portion 156 for pumping operation. For example, actuator 168 can include an internally disposed pneumatic pumping chamber or alternatively actuation can be provided by an internally disposed piezoelectric or shape memory material having an electric, thermal or magnetically induced dimension change to move body portion 158 relative to body portion 156.

Figure 10:
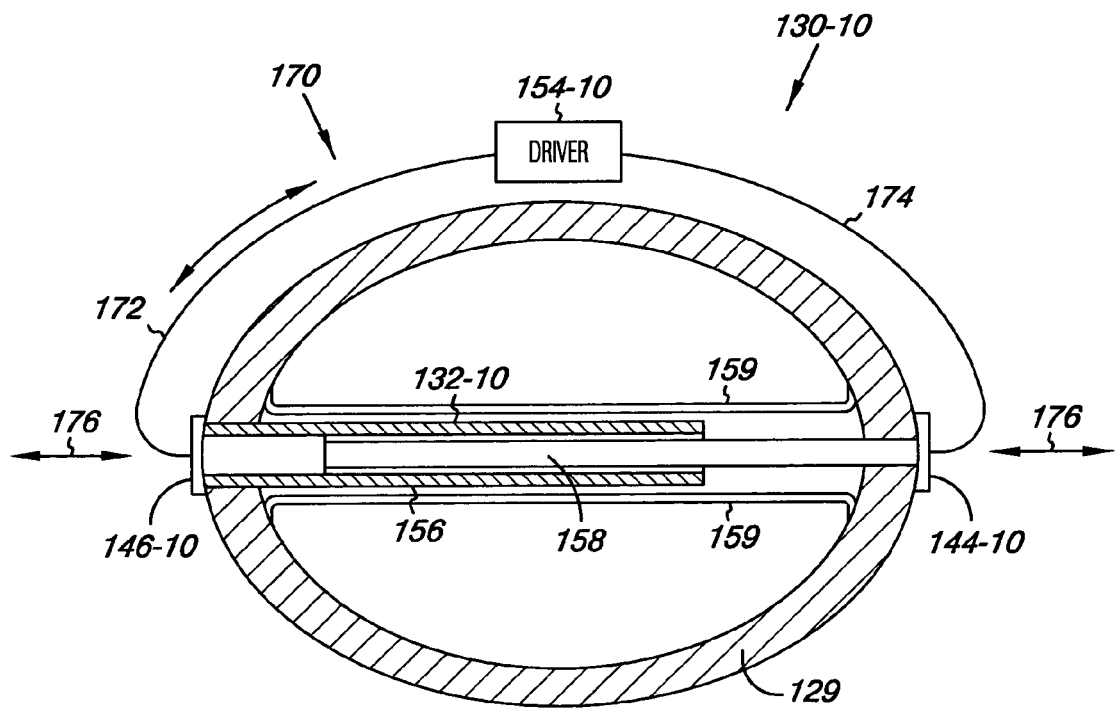
Figure 11:
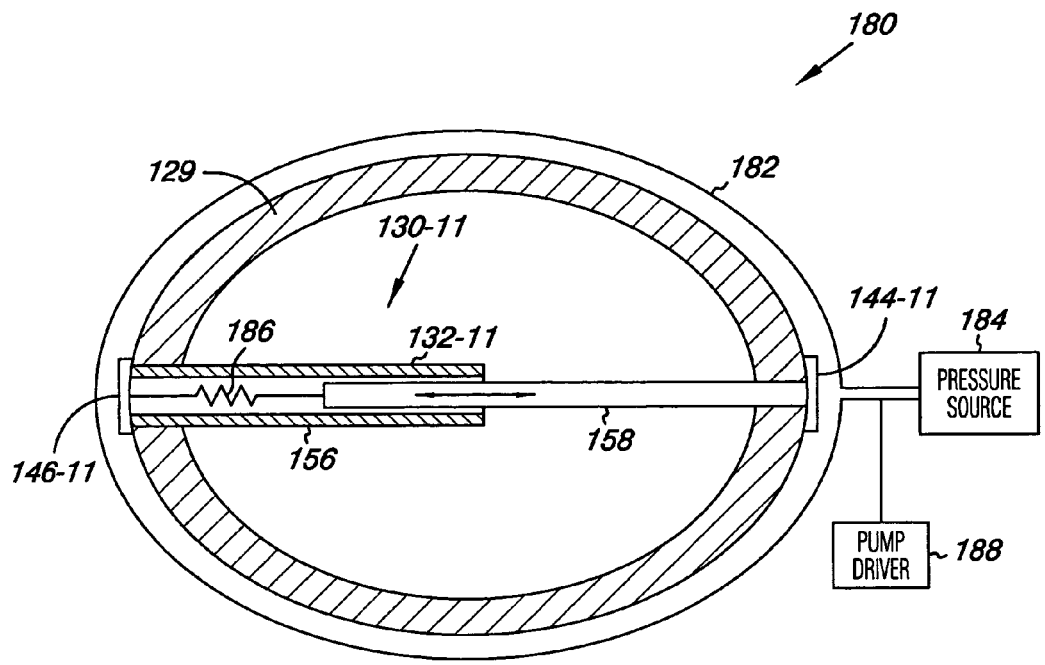

FIGS. 10-11 illustrate alternate embodiments of a ventricular assist device including an elongate body having first and second body portions slideably relative to one another and an actuation assembly which supplies an actuation force to opposed ends of the elongate body to slidably adjust the first and second body portions for pumping operation, where like numbers are used to refer to like parts. In particular, in the embodiment illustrated in FIG. 10, opposed forces are supplied by a via clamp assembly 170 having opposed arm portions 172, 174 which supply force to opposed ends or portions of the elongate body 132-10 to slidably adjust body portions 156, 158. An optional blood-contact sheath 159 may be used with any of the embodiments of the present invention. Blood-contact sheath 159 isolates the mating and sliding components of device 130 from blood and may bend, fold, stretch, compress, or accordion to provide a smooth continuous blood-contact surface.

As shown, arm portions 172, 174 of the clamp assembly 170 move towards or away from one another as illustrated by arrows 176 via driver 154-10 (illustrated schematically) to open and close arm portions 172, 174 of the clamp assembly 170 for pumping operation. In an example embodiment, driver 154-10 can be formed of a piezoelectric or shape memory material which, when energized electrically, thermally or magnetically expands and contracts to open and close arm portions 172, 174 of the clamp assembly 170 for pumping operation. Alternatively, driver 154-10 can be a pneumatic, hydraulic or electrically driven device which moves arm portions 172, 174 along an actuation stroke.

In an embodiment illustrated in FIG. 11, the ventricular assist device 130-11 includes first and second body portions 156, 158 which are pneumatically actuated via a pneumatic actuator assembly 180. The pneumatic actuator assembly 180 includes a bladder 182 which is disposed about the ventricle chamber and aligned with opposed ends of the elongate body 132-11 to slidably adjust the body portions 156, 158 to expand and contract the length dimension of the elongate body 132-11 for pumping operation. As shown, pressure is supplied to the bladder 182 from a pressure source 184 as illustrated diagrammatically to fill the bladder 182 for pumping operations.

Pressure is selectively supplied via a pump or driver 188 (illustrated diagrammatically) to operate the ventricular assist device 130-11 as described. In the illustrated embodiment of FIG. 11, body portion 158 is biased by spring assembly 186 in an extended position and is slidably contracted via expansion of bladder 182. Pressure is selectively or controllably released from the bladder 182 to extend the elongate body 132-11 for pumping operation, although application is not limited to a spring biased assembly as shown.

Figure 12:
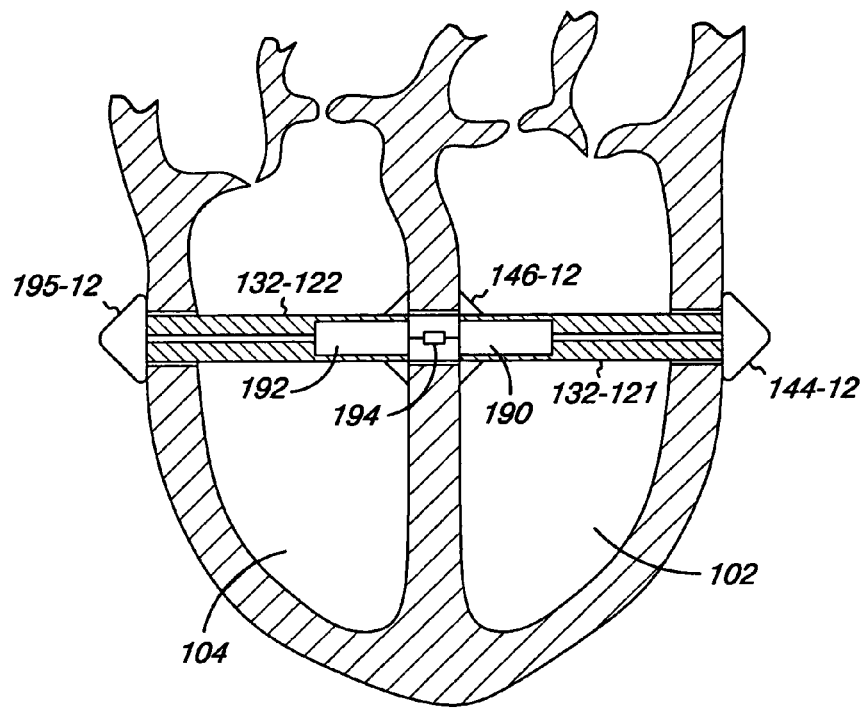
FIG. 12 illustrates an embodiment of ventricular assist device operable to provide cardiac assistance to a damaged ventricle chamber using a healthy ventricle chamber.

FIG. 12 illustrates an embodiment of a ventricular assist assembly which is powered by operation of a healthy ventricle chamber. In particular, contraction or expansion of the healthy chamber (i.e., ventricle 104) is transferred to assist contraction or expansion of a damaged ventricle chamber 102.

In the embodiment illustrated in FIG. 12, the assembly includes an elongate body 132-121 being compressible between ventricle anchors 144-12 and 146-12 during compression of diseased ventricle chamber 102 and being coupled to energy output means 190. The assembly also includes an elongate body 132-122 being compressible between ventricle anchors 146-12 and 195-12 during compression of healthy ventricle chamber 104 and being coupled to energy input device 192. The assembly or embodiment further includes an energy transfer device or means 194. Energy transfer device 194 can be located at least in part within the heart as shown, or can be located external to the heart. Energy input device 192, energy transfer device 194, and energy output device 190 can utilize pneumatic, hydraulic, mechanical, electric, or magnetic energy.

In use, systolic muscle compression of healthy ventricle 104 compresses elongate body 132-122, actuating energy input means or device 192 which transfers energy via energy transfer means or device 194 to energy output means or device 190 which applies force to compress elongate body 132-121 thereby applying compressive force to aid compression of diseased ventricle 102. As shown in FIG. 12, elongate bodies 132-121 and 132-122 can be configured as a single device with opposed aspects of ventricle anchor 146-12 being used in common. Alternatively, elongate bodies 132-121 and 132-122 can be separate devices requiring two separate ventricle anchors 146-12. The separate devices allow elongate bodies of the devices to be located and oriented advantageously in particular regions of ventricles 102 and 104 which will provide the most effective ventricle assistance.

Figure 13:
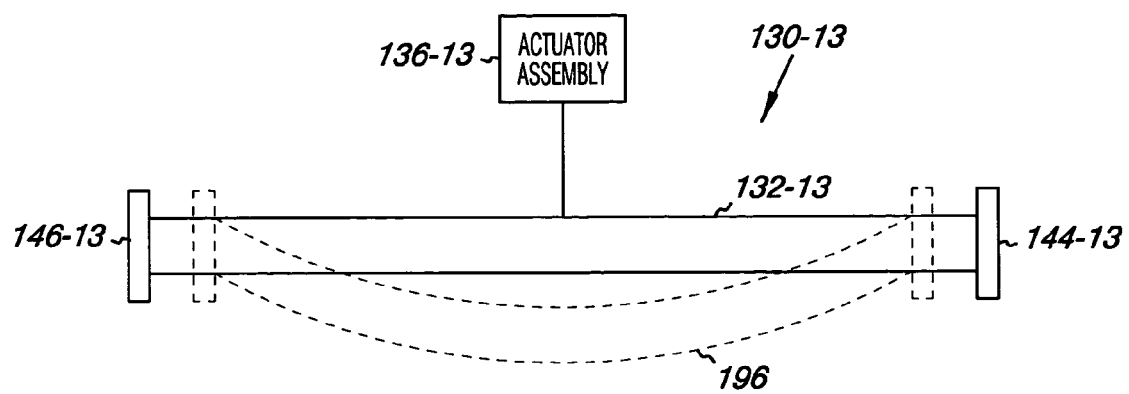
FIGS. 13-14 schematically illustrate alternate embodiments of a ventricular assist device having a flexible body.

FIG. 13 illustrates an alternate embodiment of a ventricular assist device 130-13. In the illustrated embodiment, the ventricular assist device 130-13 is formed of an elongate body 132-13 having a flexible or bendable length as illustrated by dotted lines 196 between ventricle anchors 144-13, 146-13. The elongate body 132-13 is bent or flexed to adjust a length dimension between the ventricle anchors 144-13, 146-13 via actuator assembly 136-13 to provide pumping operation.

Figure 14:
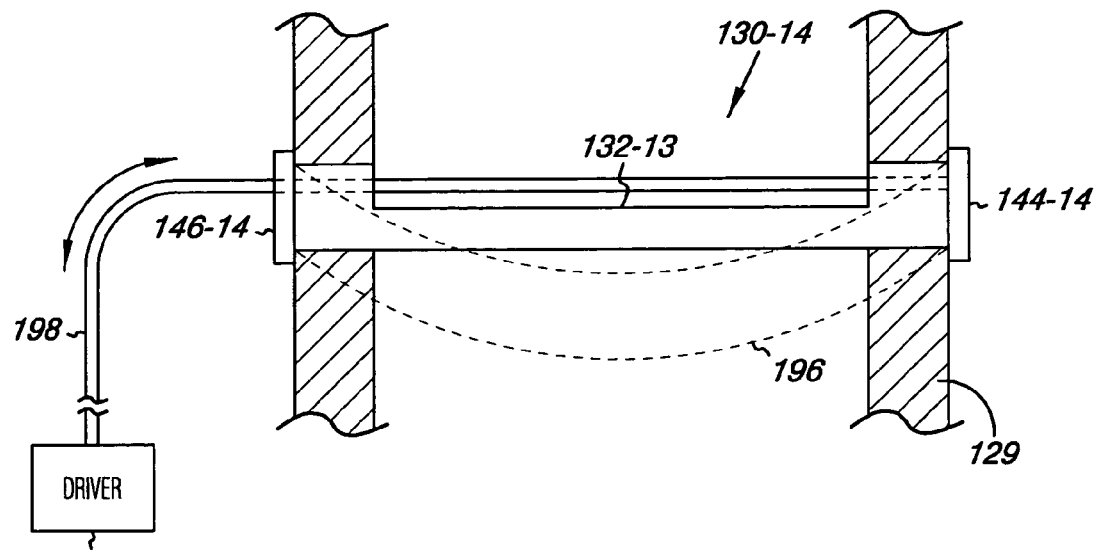

FIG. 14 illustrates an embodiment of an actuation assembly or system to flex or bend the flexible elongate body 132-13 for pumping operation. As shown, the assembly includes a cable 198 fixedly coupled to a ventricle anchor 144-14 and slidably coupled to ventricle anchor 146-14. Cable 198 is moved along an actuation stroke via driver 154-14 as illustrated schematically to intermittently flex or bend the elongate body 132-13 for pumping operation. The driver 154-14 can be powered electrically, pneumatically, hydraulically or magnetically and although a particular, actuator assembly is illustrated, application is not limited to the particular actuation assembly illustrated.

Figure 15:
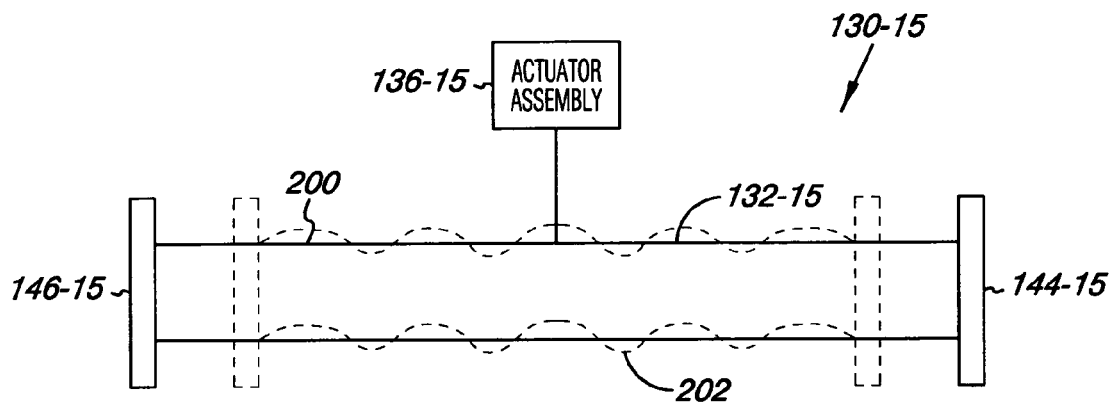
FIGS. 15-16 schematically illustrate alternate embodiments of a ventricular assist device having a collapsible body

In an alternate embodiment illustrated in FIG. 15, ventricular assist device 130-15 includes an elongate body 132-15 formed of a collapsible tube 200. The collapsible tube 200 provides a collapsible length dimension between ventricle anchors 144-15, 146-15 as illustrated schematically by dotted lines 202. The collapsible tube or structure is normally biased in an extended or non-collapsed condition and is intermittently collapsed by actuator assembly 136-15 for pumping operation. Alternatively, the actuator assembly intermittently extends and collapses the collapsible elongate body for pumping operation.

Figure 16:
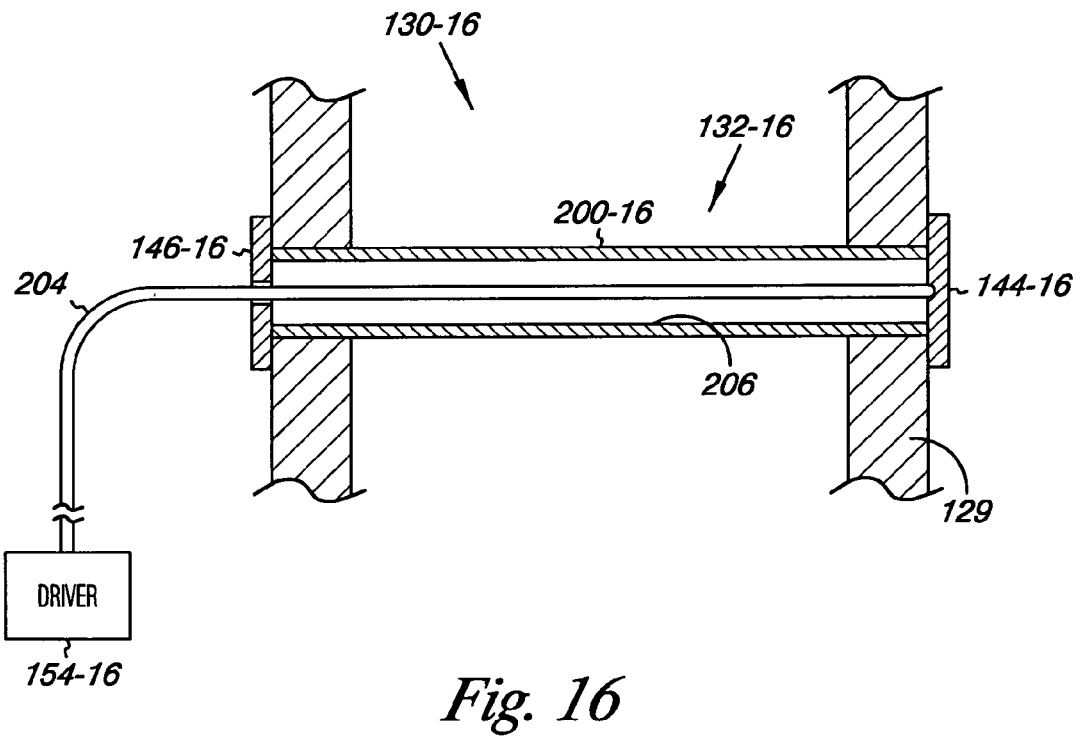

FIG. 16 illustrates an embodiment of an actuator assembly for collapsing a collapsible elongate body 132-16 having a collapsible length dimension between ventricle anchors 144-16, 146-16 for pumping operation. In particular, the actuator assembly includes cable 204 fixed to ventricle anchor 144-16 and slidable relative to ventricle anchor 146-16. In the illustrated embodiment, cable 204 extends through lumen 206 of the collapsible tube 200-16 of elongate body 134-16 and is movable along an actuation stroke via driver 154-16 to collapse (and/or expand) tube 200-16 for pumping operation.

Figure 17:
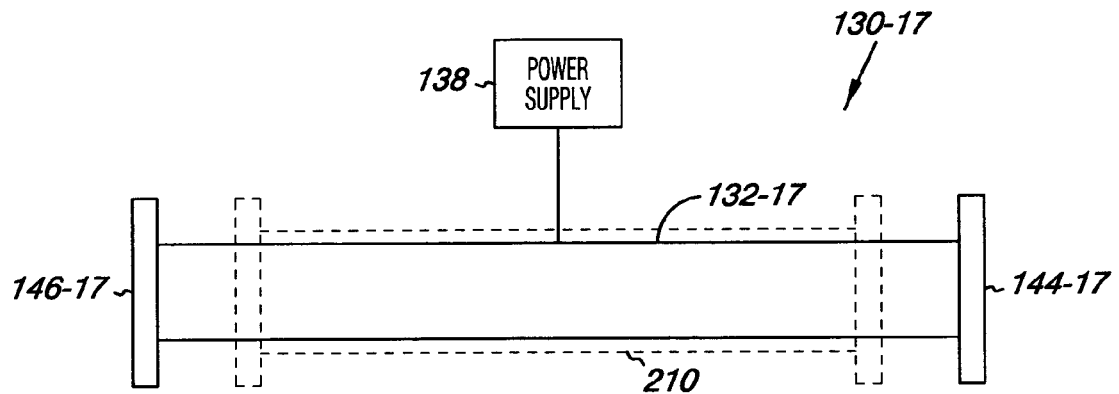
FIG. 17 illustrates an embodiment of a ventricular assist device including an elongate body having an energizable dimension change.

FIG. 17 illustrates an alternate embodiment of a ventricular assist device 130-17 including an elongate body 132-17 having an adjustable length dimension. In the embodiment shown in FIG. 17, the elongate body 132-17 is formed of a material which has an electrical, thermal or magnetically induced dimension change so that energization of the elongate body 132-17 or portion thereof by a power supply 138 provides an adjustable length dimension as illustrated by dotted lines 210 of FIG. 17. In particular, the length of the elongate body 132-17 can be expanded or contracted between ventricle anchors 144-17 and 146-17 via energization of the material to provide intermittent pumping operation.

Figure 18:
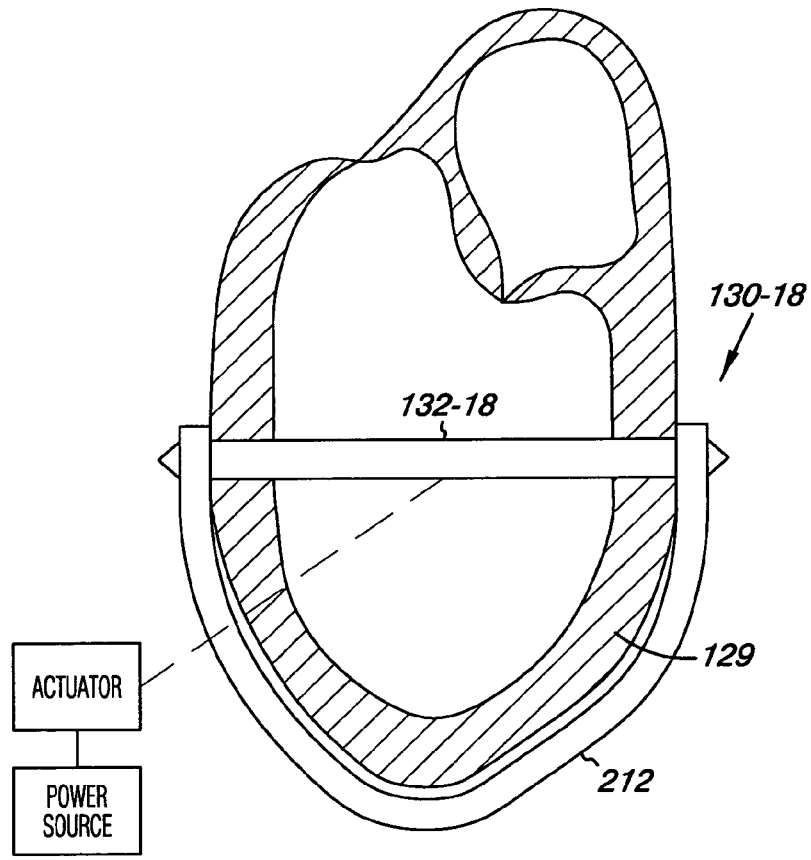
FIGS. 18-19 illustrate alternate embodiments of a ventricular assist device including an elongate body having an adjustable length dimension between opposed ventricle wall portions.
Figure 19:
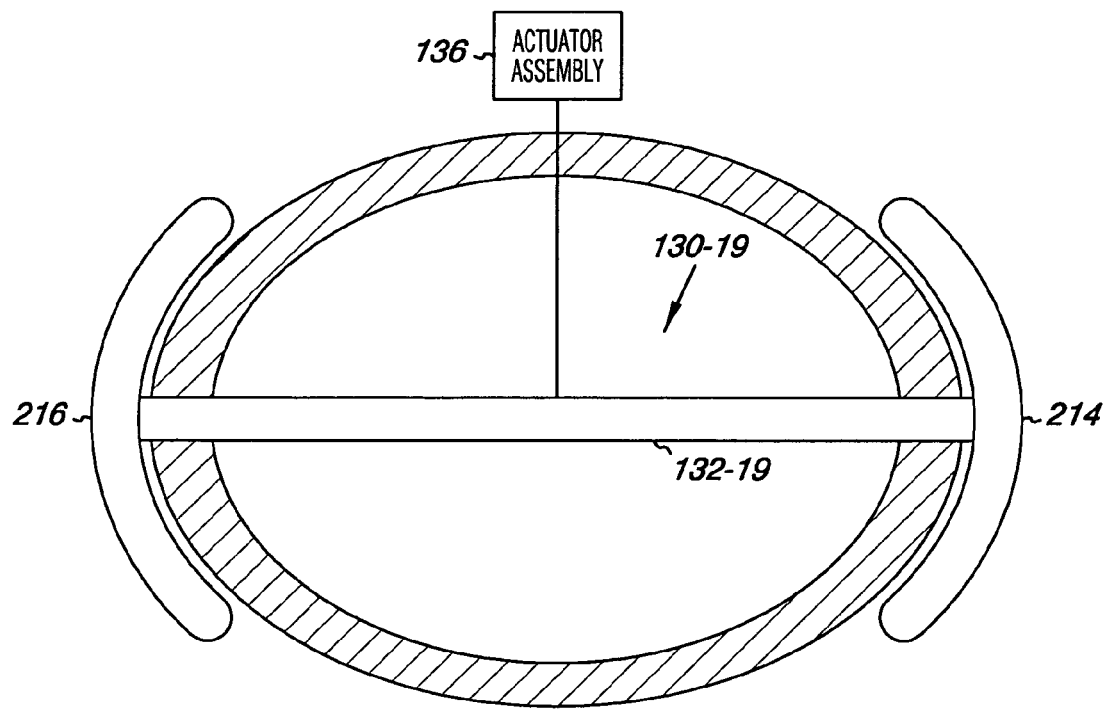

FIG. 18-19 illustrate alternate ventricular assist device embodiments including an elongate body having an adjustable length dimension as illustrated by the dotted lines. In particular, in the embodiment illustrated in FIG. 18, the ventricular device 130-18 includes a "U" shaped plate or portion 212 which is coupled to opposed end portions of the elongate body 132-18 to transfer or distribute force to the ventricle wall via expansion or contraction of the elongate body 132-18 as previously described.

In one embodiment, the "U" shaped plate 212 normally biases the ventricle chamber in an expanded profile and is actuated to compress the chamber for pumping operation. In another embodiment illustrated in FIG. 19, the ventricular assist device 130-19 includes opposed curved shaped plates 214, 216 coupled to opposed end portions of elongate body 132-19 (having an adjustable length dimension) and movable therewith to assist with pumping operations of the ventricle chamber.

Figure 20:
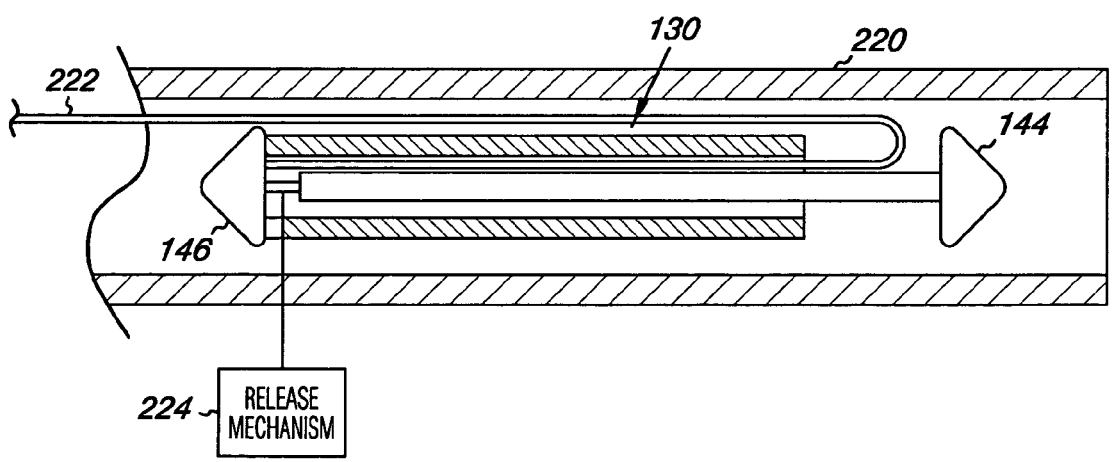
FIGS. 20-21 schematically illustrate an embodiment for percutaneous transluminal deployment of embodiments of the ventricular assist device.
Figure 21:
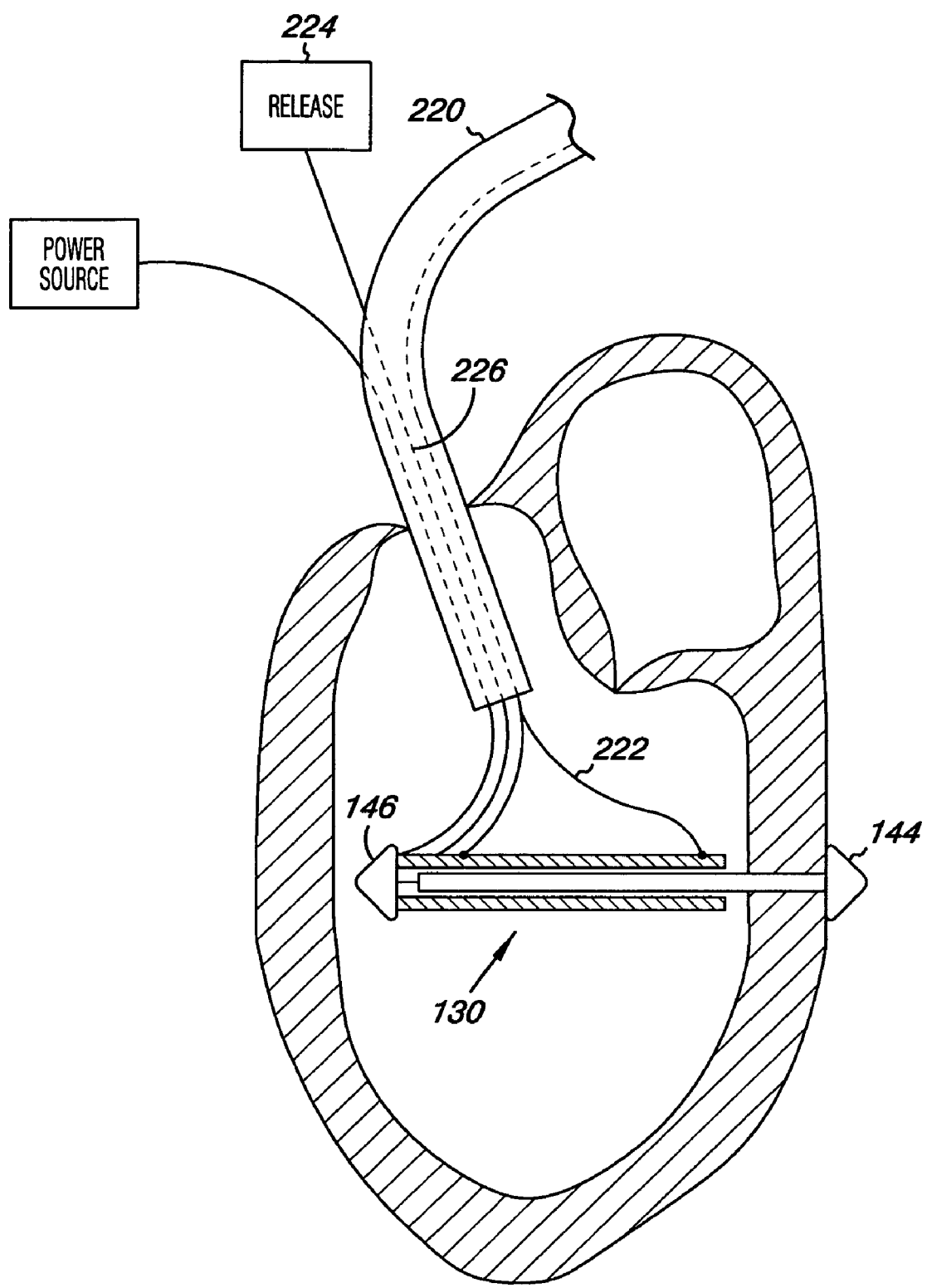

Embodiments of the ventricular assist device 130 can be surgically implanted or percutaneously intravascularly inserted for less invasive deployment. In particular, as schematically illustrated in FIGS. 20-21, the ventricular assist device 130 is inserted in a collapsed profile via catheter 220. As shown in FIG. 21, the device is released from the catheter 220 for deployment. The device is remotely controlled via a tether assembly 222. In the embodiment shown, a first end of the device (ventricle anchor 144) is secured to a first ventricle wall portion and thereafter, the device is expanded via operation of a release mechanism 224 to deploy the opposed end of the device (for example, ventricle anchor 146) into a second opposed ventricle wall portion.

The release mechanism 224 can be a mechanical, magnetic or electric mechanism and can be remotely controlled or controlled via an intravascular connection as illustrated by dotted line 226 in FIG. 21. In particular, the mechanism 224 can be magnetically released or released by force or electrical current and application is not limited to any particular design. Once deployed, expansion and contraction of the elongate body is controlled via operation of an actuator (internal or external) coupled to a remote power source or internal power source. Should cardiac assistance no longer be necessary, the ventricular assist device described can be used as a passive support to limit distension of the ventricle walls or chamber.

The embodiments shown in FIGS. 18-19 can be modified as illustrated in FIG. 22. FIG. 22 depicts an external "U" shaped member 212-22 coupled to the ventricle by ventricle anchors 144-22 and 146-22 but which does not span the inside of the ventricle between ventricle anchors 144-22 and 146-22. A power source 138 and actuator 136-22 cause flexing of member 212-22 to form an elongate body actuatable to compress or expand the ventricle. Ventricle anchors 144-22 and 146-22 may pass all the way through the ventricle walls 129 as shown, or partway through, or be attached to the outer surface; through rivet-type 300, helied wire type 302, patch and suture type 306, or other anchor, or an adhesive or thermal bond, as schematically illustrated in FIGS. 22-1, 22-2, and 22-3.

Although the present invention has been described with reference to preferred embodiments, workers skilled in the art will recognize that changes may be made in form and detail without departing from the spirit and scope of the invention.

What is claimed is:

1. A ventricular device comprising:
    a first ventricle anchor and a second ventricle anchor anchorable to opposed ventricle wall portions; and
    a ventricle body positioned entirely between the first ventricle anchor and the second ventricle anchor and extending between and terminating at the first ventricle anchor and the second ventricle anchor where the ventricle body includes a first body portion of fixed length extending from the first ventricle anchor and a second body portion of fixed length extending from the second ventricle anchor that is positioned in an extended configuration partially within a lumen of the first body portion, wherein a portion of the first body portion and a portion of the second body portion each are configured to extend through one of the opposed ventricle wall portions, and wherein the first body portion and the second body portion are slideable relative to one another to reversibly expand and collapse between a first length dimension and a second smaller dimension to provide cardiac assistance.

2. The ventricular device of claim 1 wherein the ventricle body includes the first body portion coupled to the first ventricle anchor of the opposed spaced ventricle anchors and the second body portion slidably coupled to the first body portion and coupled to the second ventricle anchor of the opposed spaced ventricle anchors to allow the ventricle body to reversibly expand and collapse between the first length dimension and the second smaller dimension.

3. The ventricular device of claim 2 and further comprising a cable coupled to the second body portion to slidably adjust the second body portion relative to the first body portion to reversibly expand and collapse the ventricle body between the first length dimension and the second smaller dimension.

4. The ventricular device of claim 1 and further comprising at least one ventricle plate coupled to an end portion of the ventricle body.

5. The ventricular device of claim 4 including a plurality of ventricle plates including a first ventricle plate coupled to one end portion of the ventricle body and a second ventricle plate coupled to an opposed end portion of the Ventricle body.

6. The ventricular device of claim 4 wherein the ventricle plate is generally "U" shaped and includes a first end coupled to one end portion of the Ventricle body and a second end coupled to an opposed end portion of the Ventricle body.

7. The ventricular device of claim 1 and further comprising an actuator assembly coupled to the Ventricle body to reversibly expand and collapse the ventricle body between the first length dimension and the second smaller dimension.

* * * * *